(12) United States Patent
Bourne et al.

(10) Patent No.: US 10,258,709 B2
(45) Date of Patent: Apr. 16, 2019

(54) SCENT DIFFUSER WITH INTEGRATED AIR CIRCULATOR

(71) Applicant: Energizer Brands II, LLC, St. Louis, MO (US)

(72) Inventors: Chris Bourne, Stansbury Park, UT (US); Kathy Rasmussen, Draper, UT (US)

(73) Assignee: Energizer Brands II, LLC, St. Louis, MO (US)

( * ) Notice: Subject to any disclaimer, the term of this patent is extended or adjusted under 35 U.S.C. 154(b) by 86 days.

(21) Appl. No.: 15/586,060

(22) Filed: May 3, 2017

(65) Prior Publication Data

US 2018/0318462 A1   Nov. 8, 2018

(51) Int. Cl.
*A61L 9/00* (2006.01)
*B01F 3/04* (2006.01)
*A61L 9/12* (2006.01)

(52) U.S. Cl.
CPC .................. *A61L 9/122* (2013.01); *A61L 9/00* (2013.01); *A61L 9/12* (2013.01); *A61L 9/127* (2013.01); *B01F 3/04085* (2013.01); *A61L 2209/11* (2013.01)

(58) Field of Classification Search
CPC ..................................... B01F 3/04; A61L 9/00
USPC ...... 422/124; 261/30, 84, DIG. 88, DIG. 89, 261/107
See application file for complete search history.

(56) References Cited

U.S. PATENT DOCUMENTS 5,480,591 A * 1/1996 Lagneaux ................. A61L 9/12
261/104
2002/0197189 A1* 12/2002 Lua .......................... A61L 9/122
422/124

* cited by examiner

*Primary Examiner* — Robert A Hopkins
(74) *Attorney, Agent, or Firm* — Alston & Bird LLP

(57) ABSTRACT

A scent diffuser (e.g., air freshener) configured to automatically circulate fragrant air throughout a surrounding environment comprises a powered air circulator configured for circulating air and a fragrance composition throughout the surrounding environment, and a solar cell positioned within a support face of the air circulator. The support face is configured to secure the scent diffuser relative to a support surface and has an open portion configured to allow light to contact the solar cell. The air circulator may comprise a centrifugal fan positioned within the housing and configured to draw air through intake apertures in sidewalls of the housing and to exhaust air and fragrance through an outflow aperture of the housing.

19 Claims, 6 Drawing Sheets

SCENT DIFFUSER WITH INTEGRATED AIR CIRCULATOR

BACKGROUND

Scent diffusers (e.g., air fresheners) may comprise entirely passive configurations, such as fragrance-saturated paper panels that rely on externally generated air movement to circulate evaporating fragrance-composition throughout an environment. Automobile interiors are particularly well-suited for such passive scent diffuser configurations, because automobile owners and operators generally desire small, minimally invasive scent diffusers that do not significantly obstruct the automobile operators' line of vision while operating the vehicle. However, the functionality of passive scent diffusers is limited when the vehicle is not in operation, and therefore the vehicle is not circulating air throughout the vehicle interior and past the air diffuser.

Accordingly, a need exists for a scent diffuser configuration that disseminates a desired fragrance throughout an automobile interior regardless of whether the automobile is circulating air through the automobile interior.

BRIEF SUMMARY

Various embodiments are directed to an active scent diffuser comprising a fragrance reservoir (storing fragrance composition therein), an air circulator, and a power source. The air circulator is configured to circulate a fragrance composition (e.g., an evaporated fragrance composition, an atomized fragrance composition, a sublimated fragrance composition, and/or the like) emitted from the fragrance reservoir. The power source may comprise a battery and a battery charger, such as an integrated solar cell positioned on a back support surface of the scent diffuser, that collectively powers the air circulator continuously, periodically, and/or the like. The active scent diffuser may additionally comprise an onboard computing entity (e.g., a circuit board with integrated logic components) with an integrated power switch for automatically powering the air circulator on and/or off. The active scent diffuser may also comprise a support component configured to secure the active scent diffuser in a desired location. For example, the support component may comprise a tacky plate configured to secure (e.g., detachably secure) the back support surface of the scent diffuser to an automobile interior surface, such as the interior surface of an automobile window (e.g., windshield).

Various embodiments are directed to a scent diffuser configured to be secured relative to a support surface and configured to circulate air and fragrance throughout a surrounding environment. In certain embodiments, the scent diffuser comprises a powered air circulator configured for circulating air and fragrance composition throughout the surrounding environment; and a solar cell positioned within a support face of the air circulator, wherein the support face is configured to secure the scent diffuser relative to a support surface, and wherein the solar cell is configured to convert energy from the light into electrical energy for use by the powered air circulator.

Certain embodiments are directed to a scent diffuser comprising: a housing defining a body portion and a support face, wherein the support face is configured to support the scent diffuser on a support surface; a fragrance composition stored within the housing; a powered air circulator, such as a powered centrifugal fan, configured to circulate at least a portion of the fragrance composition through a surrounding environment; and a power supply. In certain embodiments, the power supply comprises an electrical storage device in electrical connection with the powered air circulator; and a solar cell positioned within the support face, wherein the solar cell is configured to convert light energy passing through the support surface into electrical energy and to charge the electrical storage device with the electrical energy.

In various embodiments, the support face comprises one or more tacky portions configured to detachably adhere the scent diffuser against the support surface (e.g., a window). Moreover, the housing may define one or more intake apertures and an outflow aperture (e.g., an at least partially open front portion opposite the support face), and wherein the air circulator is configured to intake air into the housing through the one or more intake apertures and to flow the intake air over at least a portion of the fragrance composition to produce fragrant outflow air and substantially flow the fragrant outflow air through the at least one outflow aperture.

Moreover, certain embodiments of the scent diffuser comprise a controller circuit configured to monitor a charge level of the electrical storage device; and upon detecting that the charge level of the electrical storage device satisfies a charge criteria, close an electrical circuit between the electrical storage device and the powered air circulator to activate the powered air circulator. In various embodiments, the controller circuit is configured to maintain the closed electrical circuit until the charge level of the electrical storage device reaches a predefined threshold.

Certain embodiments are directed to a scent diffuser comprising a housing comprising one or more sidewalls and an at least partially open front portion, wherein the one or more sidewalls have one or more intake apertures extending therethrough; a fragrance composition stored within the housing; and a centrifugal fan aligned with the one or more intake apertures, wherein the centrifugal fan is configured to intake air into the housing through the one or more intake apertures and to flow the intake air over at least a portion of the fragrance composition to produce fragrant outflow air and to substantially flow the fragrant outflow air through the at least partially open front portion.

In certain embodiments, the fragrance composition is a liquid stored within a fragrance reservoir comprising a wicking surface, wherein the fragrance reservoir is positioned at least partially within the housing, and wherein the wicking surface is configured to allow the fragrance composition to evaporate therefrom into the intake air. In certain embodiments, the centrifugal fan directs air between lateral edges of the fragrance reservoir and interior edges of the at least partially open front portion of the housing.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

Figure 1:
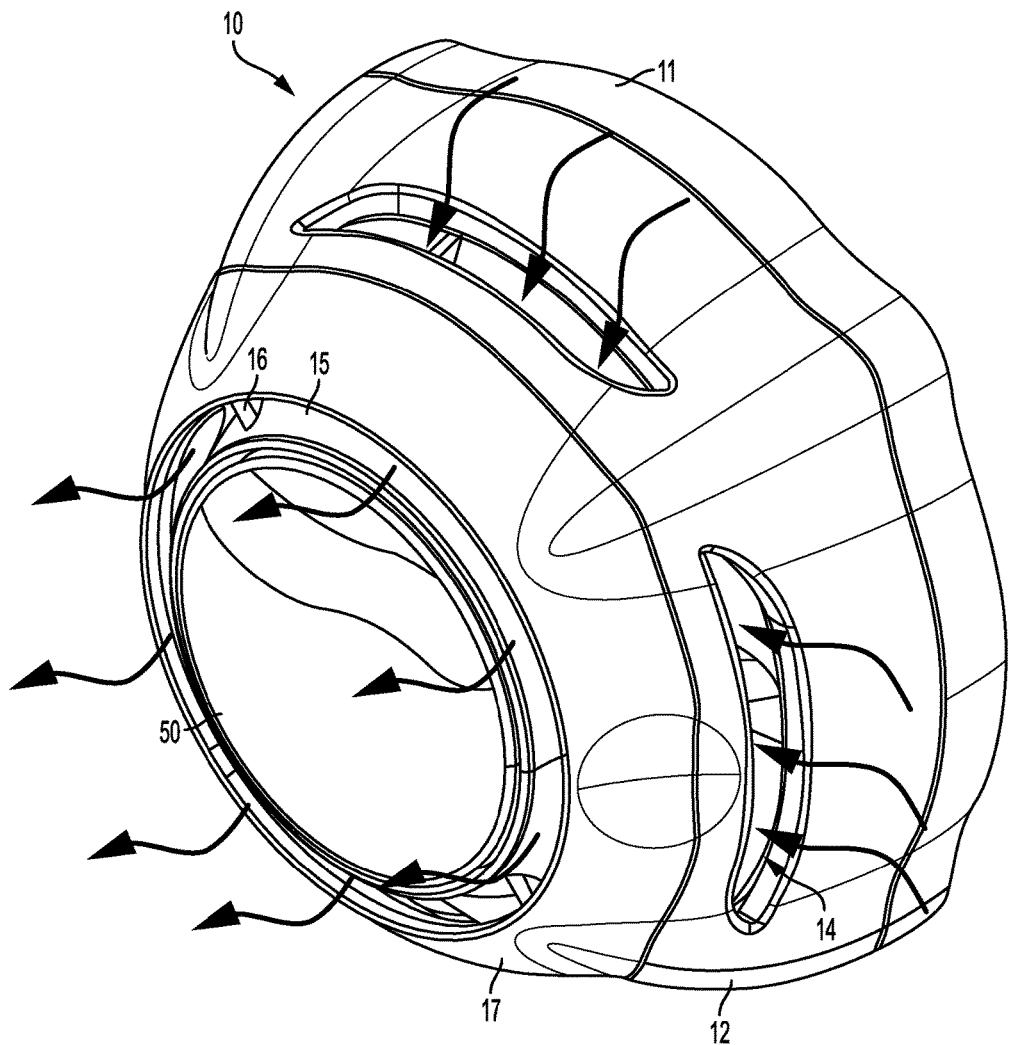
FIG. 1 is a front perspective view of a scent diffuser according to one embodiment.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

Various embodiments are directed to a scent diffuser (e.g., an air freshener) having an integrated air circulator for circulating a fragrance composition throughout an environment surrounding the scent diffuser. For example, the scent diffuser may be secured within a vehicle interior, and the scent diffuser may automatically circulate fragrant air comprising a fragrance composition (e.g., an evaporated fragrance composition, an atomized fragrance composition, a sublimated fragrance composition, and/or the like) throughout the vehicle interior. The air circulator may comprise a powered fan (e.g., a fan driven by an electric motor) selectively powered by a power supply via an automatically controlled power switch within an integrated circuit. The power supply may comprise an electrical storage device (e.g., a battery) and/or an onboard battery charger (e.g., a solar cell). The scent diffuser may be configured for autonomous operation via the onboard switch, which may selectively direct electrical current from the electrical storage device to the powered fan to circulate air and fragrance composition throughout the environment surrounding the scent diffuser.

The attached figures illustrate a scent diffuser 10 according to one embodiment. As shown in the perspective view of a scent diffuser 10 of FIG. 1, the scent diffuser 10 comprises a housing surrounding various components of the scent diffuser 10 to provide an integrated active scent diffuser configuration. As shown, the housing may have an at least substantially rectangular (e.g., square) shape, having convex curved sidewalls and rounded corners between adjacent sidewalls. However, it should be understood that the scent diffuser 10 housing may have any of a variety of shapes, such as circular, ovular, square, rectangular, octagonal, hexagonal, triangular, and/or the like.

Moreover, the housing sidewalls may collectively form an at least substantially cubical shape, such that a front portion of the housing (e.g., adjacent fragrance reservoir 50, described in detail herein) has a size and shape at least substantially equal to the size and shape of the back support surface (e.g., adjacent solar cell 41, described in detail herein). However, in certain embodiments, the sidewalls of the housing may converge from the back support surface to the front portion of the housing (e.g., forming an at least substantially pyramidal frustum shape), such that the front surface of the housing has a shape at least substantially similar to the back support surface, but the size of the front surface is smaller than the size of the back support surface. In such embodiments, a portion of the interior of the housing (e.g., defined by the front body 12 and/or a front plate 17 discussed in greater detail herein) may converge toward a front opening of the housing, to thereby direct air within the housing out of exhaust vents defined within the front portion of the scent diffuser 10, as discussed in greater detail herein.

In the illustrated embodiment, the housing comprises a rear body 11, a front body 12, a rear plate 13, and a front plate 17. Each of the rear body 11, the front body 12, the rear plate 13, and/or the front plate 17 comprises a rigid material, such as a rigid plastic material (e.g., PVC, PET, and/or the like), a metal material, and/or the like.

Each of the rear body 11, the front body 12, the rear plate 13, and the front plate 17 are secured relative to one another (e.g., detachably secured) via one or more engagement mechanisms. For example, the front body 12 may be secured relative to the rear body 11 via one or more fasteners (e.g., screws, adhesives, and/or the like), via one or more interference fit components, and/or the like. As a non-limiting example, the front body 12 may comprise one or more pins, tabs, and/or the like configured to engage corresponding slots of the rear body 11 to create an interference fit therebetween. The one or more pins, tabs, and/or the like may define an enlarged terminal end having a larger diameter, cross-section, and/or the like relative to the remainder of the pin, tab, and/or the like. To create the interference fit, the enlarged terminal end may be pressed through corresponding slots having a cross-sectional area less than the enlarged terminal end of the pin, tab, and/or the like (e.g., by deforming a portion of the material surrounding the slot). Once the enlarged terminal end is passed through the slot, the enlarged terminal end may be prevented from passing back through the corresponding slot.

With reference again to the attached Figures, the rear plate 13 may likewise be secured relative to the rear body 11 via one or more fasteners and/or integrated engagement features (e.g., interference fit engagement features).

Figure 2:
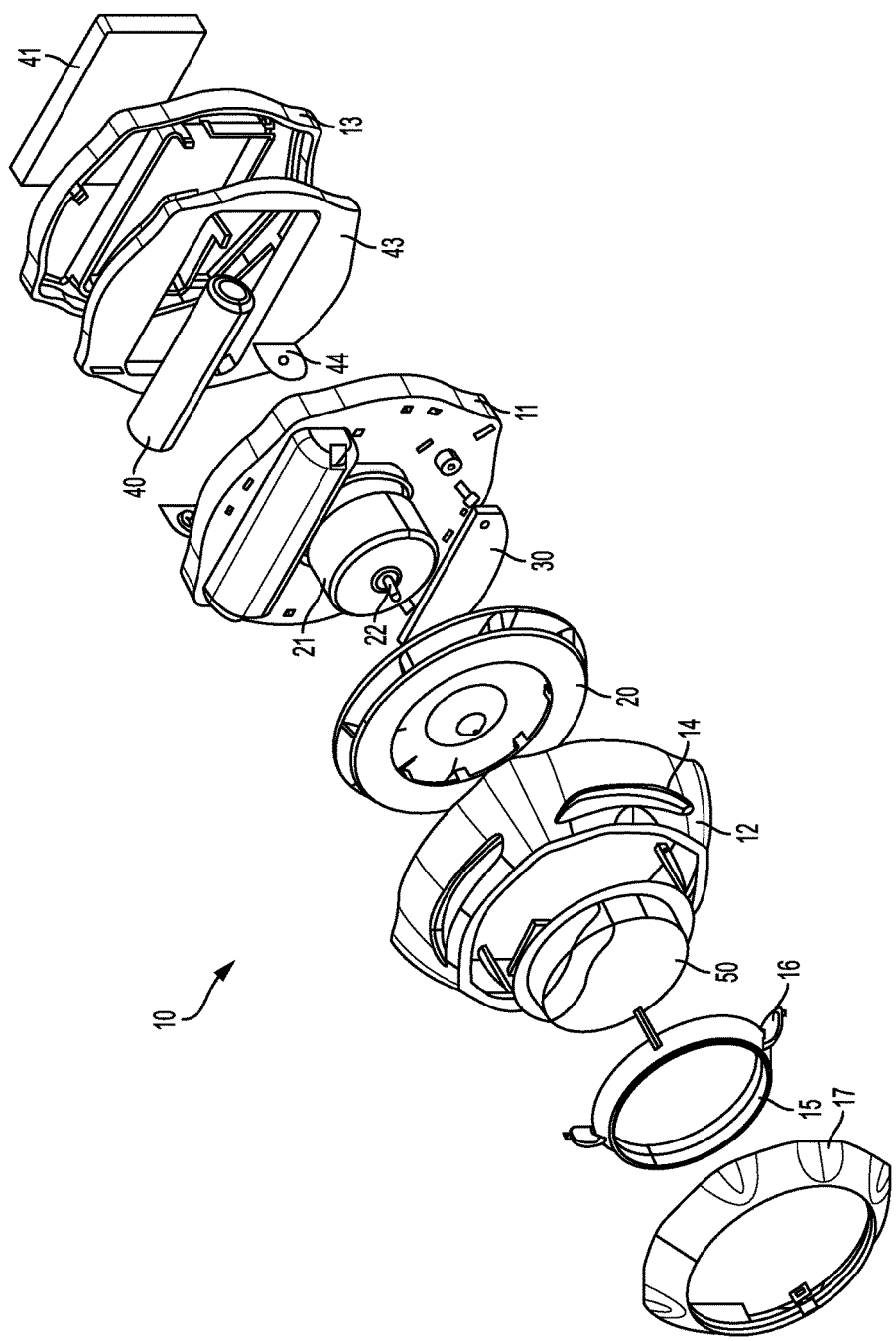
FIG. 2 is an exploded view of a scent diffuser according to the embodiment of FIG. 1.

Within the housing, the scent diffuser 10 may comprise an air circulator, a fragrance reservoir, a power supply, and a support component. As shown in the exploded view of FIG. 2 and the cutaway view of FIG. 3, the air circulator comprises a fan 20 (e.g., a centrifugal fan (also referred to as a hamster cage fan) as shown in the figures, although any of a variety of fan types may be utilized) driven by a motor 21 (e.g., an electrically driven motor).

Figure 4A:
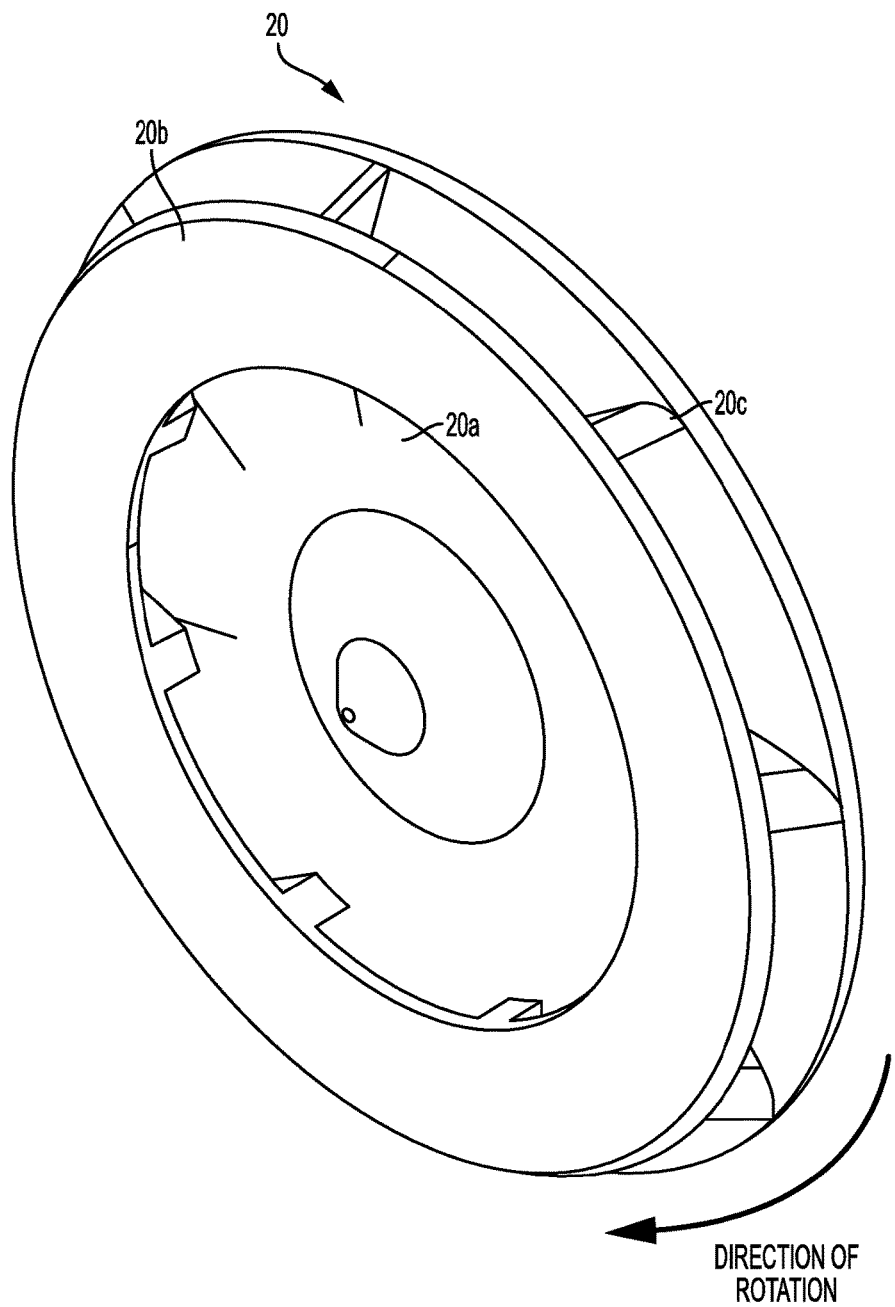
FIG. 4A is a perspective view of a fan usable within a scent diffuser according to the embodiment of FIG. 1.
Figure 4B:
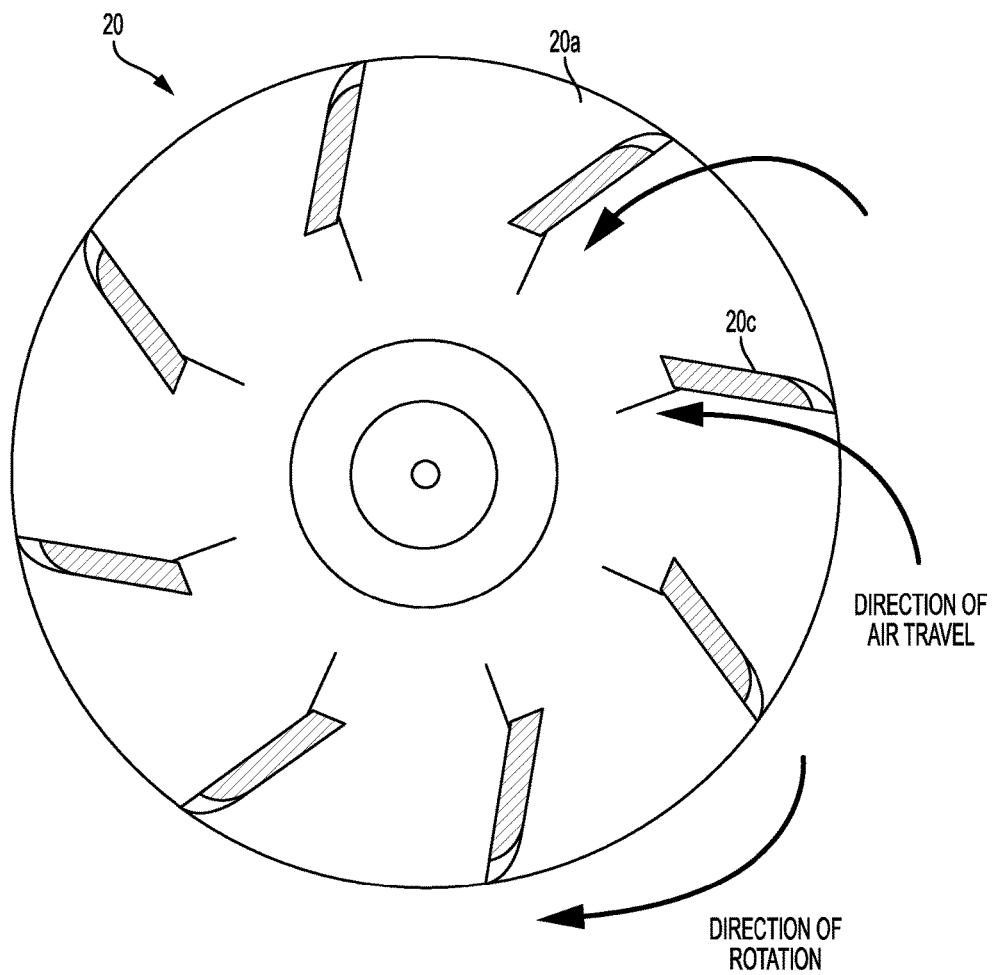
FIG. 4B is a front sectional view of a fan usable within a scent diffuser according to the embodiment of FIG. 4A.

As shown in FIGS. 4A-4B, the fan 20 may comprise a base plate 20a, an air deflector plate 20b spaced apart from the base plate 20a, and a plurality of fan blades 20c (e.g., rotary fan blades) extending between the base plate 20a and the air deflector plate 20b. The fan blades 20c may be curved and/or angled to guide air from an outside perimeter of the fan 20 toward a central portion of the base plate 20a. As shown in the front sectional view of FIG. 4B, the fan blades 20c are angled toward the direction of rotation of the fan 20 in the illustrated embodiment. Accordingly, the end of each fan blade 20c located at the outer perimeter of the fan 20 defines the leading end of each fan blade 20c during rotation. The angle of the fan blades 20c directs air along the surface of the fan blades 20c and toward the center of the base plate 20a, as indicated by the arrows shown in FIG. 4B. In certain embodiments, the angle of the fan blades 20c are sufficient to overcome centrifugal force pushing air toward the outer edge of the fan 20 such that air is pulled toward the center of the base plate 20a, and ultimately perpendicularly away from the surface of the base plate 20a as discussed herein. As just one example, the fan blades 20c may form an angle with respect to a radius extending away from the center of the base plate 20a of between about 30-45 degrees to direct air toward the center of the base plate 20a. The angle of the fan blades 20c relative to a radius of the fan 20 may be optimized for the expected run speed of the fan 20 to overcome the centrifugal force formed by the rotation of the fan 20.

As shown in FIG. 4A, the base plate 20a has a conical central portion extending away from the base plate 20a toward the plane in which the air deflector plate 20b is located. Moreover, in the illustrated embodiment of FIG. 4A, the air deflector plate 20b extends around the circumference of the base plate 20a and has an open center, thereby allowing air to pass through the open center away from the base plate 20a. Accordingly, while the fan 20 spins, air is drawn into the housing through the space defined between the base plate 20a and the air deflector plate 20b, through the fan blades 20c from the perimeter of the fan 20 and toward the center of the base plate 20a. As shown in the cutaway view of FIG. 3, the space defined between the base plate 20a and the air deflector plate 20b is aligned with and adjacent to ventilation apertures 14 within the sidewalls of the housing, such that air is drawn from the exterior of the scent diffuser 10, through the ventilation apertures 14 and into the fan 20 as discussed herein. The air is then directed along the surface of the base plate 20a, up the sides of the conical center portion, and away from the base plate 20a, through the open center portion of the air deflector plate 20b. As shown in the cutaway view of FIG. 3, the air deflects off a back surface of the fragrance reservoir 50 thereby mixing with evaporated fragrance composition to form fragrant air and moves toward side edges of the fragrance reservoir 50, where the fragrant air is redirected through an outflow aperture defined between the sides of the fragrance reservoir 50 and portions of the housing (e.g., trim ring 15 and front plate 17). The air is then directed out of the housing to be circulated through a surrounding environment through the outflow aperture defined within the front portion of the housing, between the sides of the trim ring 15 and front plate 17 (e.g., around the sides of the fragrance reservoir 50).

As shown in the figures, the fan 20 may be secured relative to a motor shaft 22 such that rotation of the motor 21 directly causes rotation of the fan 20. As shown in the cutaway view of FIG. 3, the fan 20 defines a motor shaft cavity 20d (e.g., within the conical center portion of the fan 20) extending through a back wall of the fan 20 configured to engage the motor shaft 22. Although not shown in the figures, the motor shaft 22 may define a plurality of splines extending along the length of the motor shaft 22, the plurality of splines configured to engage corresponding spline grooves in the motor shaft cavity 20d. The engagement between the motor shaft splines and corresponding spline grooves of the motor shaft cavity 20d impedes relative rotation between the fan 20 and the motor shaft 22.

In various embodiments, the fan 20 may comprise a rigid material (e.g., a rigid plastic material (e.g., PVC, PET, and/or the like), a metal material, and/or the like) and/or a flexible material (e.g., a flexible polymer material, a rubber material, and/or the like). Although not shown, it should be understood that the fan 20 may be indirectly driven by a motor 21, such as via one or more gear drives, belt drives, chain drives, and/or the like.

With reference again to the figures, the motor 21 is secured relative to the rear body 11. For example, a housing of the motor 21 is immovably secured relative to the rear body 11 (e.g., via one or more fasteners, via one or more integrated fastening mechanisms (e.g., interference fit components, friction-fit components), and/or the like), while permitting the motor internals (e.g., coils) to rotate freely within the housing.

The motor 21 is electrically secured relative to the power supply via an electronic switch. In the illustrated embodiments, the electronic switch is embodied as a controller circuit 30 on a Printed Circuit Board (PCB) that may be secured to the rear body 11 (e.g., via one or more fasteners). Although not shown, the controller circuit 30 comprises a logic controller configured to automatically determine when to electrically connect the motor 21 to the power supply (e.g., based on defined parameters). For example, the controller circuit 30 may be configured to automatically connect the motor 21 and the power supply on regular time intervals (e.g., 1 minute, 10 minutes, 1 hour, and/or the like). As yet another example, the controller circuit 30 may be configured to monitor a charge level of the electrical storage device 40, and may be configured to automatically connect the electrical storage device 40 with the motor 21 upon determining that the charge level of the electrical storage device 40 satisfies a predefined criteria. For example, the electrical storage device 40 may be placed in electrical connection with the motor 21 upon determining the charge level of the electrical storage device 40 exceeds a predefined level (e.g., based on a detected output voltage of the electrical storage device 40, based on a detected output current of the electrical storage device 40, and/or the like). Upon detecting the charge level of the electrical storage device 40 exceeds the predefined level, the controller circuit 30 may be configured to connect the electrical storage device 40 with the motor 21 to power the motor 21 until the charge within the electrical storage device 40 is reaches a predefined level (e.g., the charge level is incapable of powering the motor 21). In certain embodiments, the electrical storage device 40 may be configured to power the motor 21 for at least approximately 2 minutes on a single charge.

The defined parameters may be programmed during manufacture of the scent diffuser 10 (e.g., by hard programming of an embedded logic controller having an onboard clock) or the defined parameters may be adjustable by an end user (e.g., by adjusting a user input device (e.g., a user switch) on the scent diffuser 10). As various examples of defined parameters adjustable by a user, the controller circuit 30 may be configured to enable a user to adjust the elapsed time between motor activation periods; the elapsed time a motor remains active during a single motor activation period; the motor rotational speed during motor rotation periods, and/or the like.

Although not shown, the controller circuit 30 may be in electrical communication with the power supply to provide power to the controller circuit 30 itself. Moreover, the controller circuit 30 may be configured to control the motor 21 rotational speed, via digital or analog control of the motor 21 such that the motor and fan rotate at a predefined rotational speed (e.g., 800 RPM). For example, the controller circuit 30 may be configured to adjust the electrical current passed from the power supply to the motor 21, wherein the current level passed through the controller circuit 30 is directly proportional to the motor 21 rotational speed. As yet another example, the controller circuit 30 may be configured to utilize Pulse Width Modulation (PWM) to control the rotation speed of the motor 21. Accordingly, the controller circuit 30 may adjust the length of electrical pulses having a known current passing from the power supply to the motor 21 to control the rotation speed of the motor 21, wherein the length of each pulse is directly proportional to the rotation speed of the motor 21.

As shown in the figures, the power supply comprises an electrical storage device 40 (e.g., a secondary battery, such as a secondary AAA battery having an effective output voltage of 1.5 volts) and a solar cell 41. As shown in the figures, the electrical storage device 40 is secured within corresponding electrical contacts 44 secured within a cavity of the rear body 11. As shown, the cavity has an open side through a rear wall of the rear body 11 (e.g., on an opposite side of the rear body 11 from the connection between the rear body 11 and the motor 21 housing (e.g., secured relative to a front wall of the rear body 11)). The electrical storage device 40 may be in electrical contact with the fan motor 21 via the controller circuit 30 and may be in electrical contact with the solar cell 41 via one or more conductors (e.g., including electrical contacts 44). Accordingly, when the solar cell 41 is exposed to a light source (e.g., sunlight), the solar cell converts energy within the received light into electrical energy and passes the generated electrical energy to the electrical storage device 40 (e.g., by generating an electrical current flowing to the electrical storage device 40) to recharge the electrical storage device 40. Although not shown, the power supply may additionally comprise a charge level controller (e.g., embodied on the PCB of the controller circuit 30) configured to ensure the electrical storage device 40 is not charged beyond its capacity.

Figure 3:
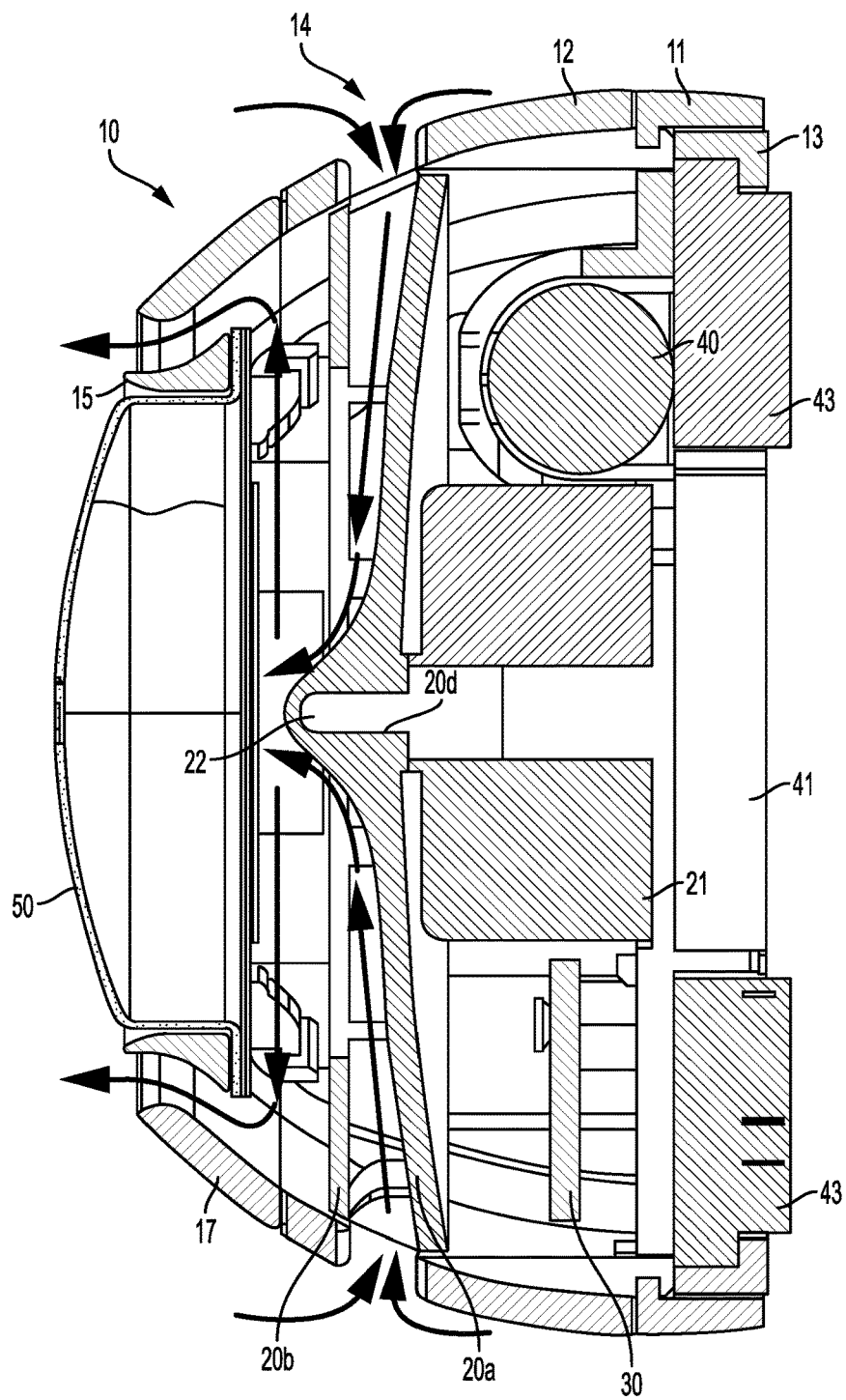
FIG. 3 is a cutaway view along a central plane of the scent diffuser shown in FIG. 1.
Figure 5:
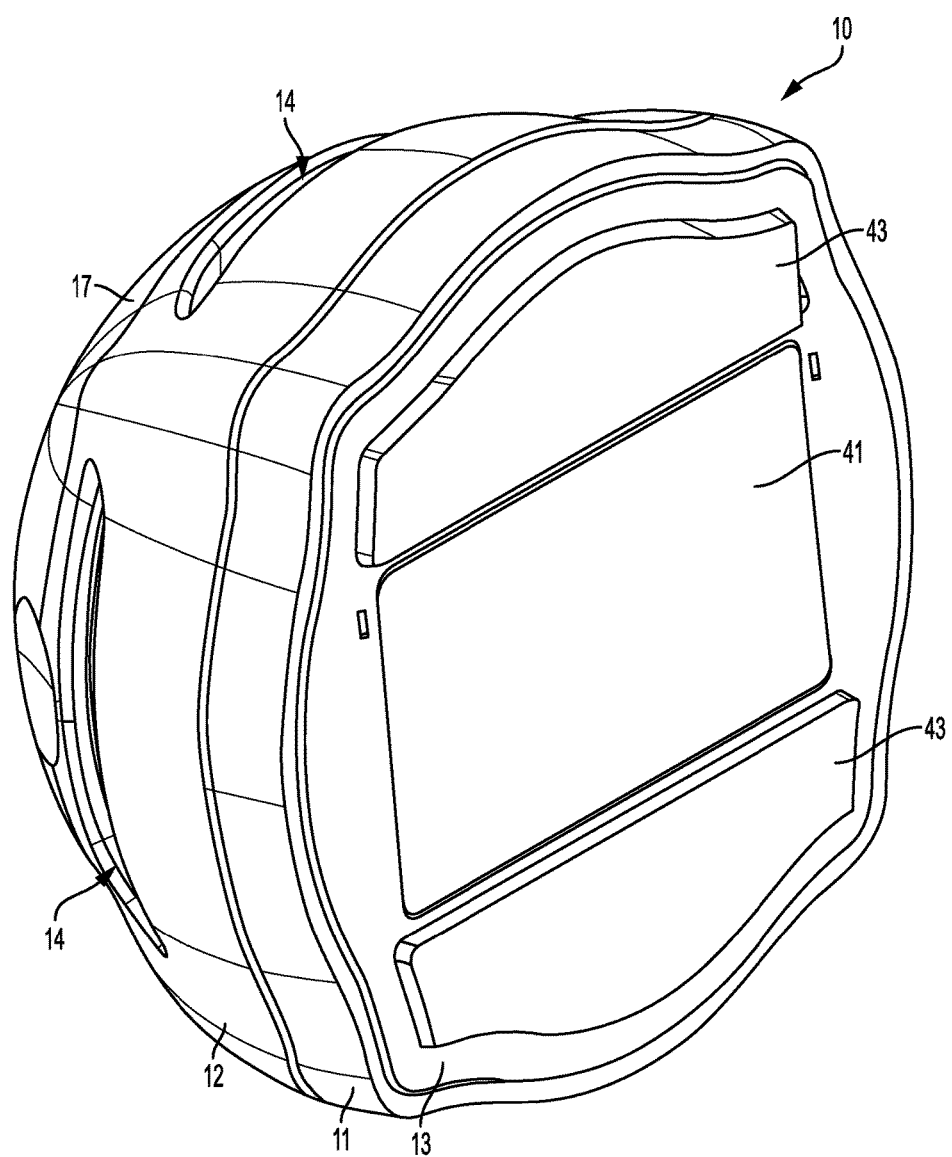
FIG. 5 is a rear perspective view of a scent diffuser according to the embodiment of FIG. 1.

As shown in the back view of the scent diffuser 10 of FIG. 5, the solar cell 41 is positioned within an aperture defined within the rear plate 13, such that the solar cell 41 is positioned within a back support surface of the scent diffuser 10 and such that light is permitted to contact the solar cell 41 (e.g., light flowing through a support surface on which the scent diffuser 10 is adhered). As shown in the cutaway view of FIG. 3, the solar cell 41 is flush with the back surface of the rear plate 13. The rear plate 13 may define a frame having a first opening configured for securing the solar cell 41 therein, and a second opening (e.g., surrounding the first opening) for one or more tacky portions of a tacky plate 43 configured for securing the scent diffuser 10 relative to various surfaces. As shown in FIG. 3, the tacky portions of the tacky plate 43 extend beyond the back surface of the rear plate 13, such that the tacky plate 43 engages a surface on which the scent diffuser 10 is to be secured, and thereby adheres the scent diffuser 10 relative to the support surface.

The tacky plate 43 may comprise a material having tacky properties, such as a tacky polyurethane having adhesive-like properties sufficient to support the weight of the scent diffuser 10 against a support surface (e.g., a vertical support surface, an angled support surface, and/or the like). Accordingly, the tacky plate 43 may be configured to provide an adhesive connection between the scent diffuser 10 and a support surface of sufficient strength to overcome shear gravitational forces acting on the scent diffuser 10 secured to a vertical surface and/or sufficient to overcome axial gravitational forces acting on a scent diffuser 10 secured to an underside of an angled support surface. For example, the tacky plate 43 may be configured to secure the scent diffuser against an interior surface of a vehicle window (e.g., side window, rear window, windshield, and/or the like). The polyurethane may be configured to be removable from a support surface while retaining tacky properties (e.g., subject to any dirt and/or debris that remains stuck to the tacky surface), such that the tacky plate 43 may be resecured against a different support surface. In certain embodiments, the tacky plate 43 may comprise an adhesive material and/or another tacky (sticky) material across at least a portion of the back support surface. The adhesive material may be configured as a one-time use material, such that the scent diffuser 10 cannot be removed from a first support surface and resecured to a second support surface.

With reference again to FIGS. 3 and 5, exposed tacky portions of the tacky plate 43 (e.g., 2 exposed tacky portions) may be positioned around the solar cell 41, such that the solar cell 41 is positioned adjacent a support surface against which the tacky plate 43 is secured. For example, when the scent diffuser 10 is secured against a window, the solar cell 41 is positioned adjacent the window such that sunlight (or other natural or artificial light) that passes through the window is absorbed by the solar cell 41 to generate electrical energy and charge the electrical storage device 40, which in turn powers the controller circuit 30 and the motor 21.

Moreover, with reference again to the figures, the housing (e.g., front body 12) has one or more (e.g., a plurality) ventilation apertures 14 defined therein. As shown in the figures, the ventilation apertures 14 may be defined through sidewalls of the front body 12, and may resemble slots extending across corresponding sidewalls of the front body 12. The plurality of ventilation apertures 14 may comprise intake apertures and/or exhaust apertures for air circulated through the fan 20 positioned within the housing. In certain embodiments, each of the ventilation apertures 14 may operate at least in part as both an intake aperture and an outflow aperture. Moreover, as discussed above, the ventilation apertures 14 may be aligned around the perimeter of the housing, and may be aligned with the fan 20, such that the fan 20 draws air through the ventilation apertures 14 and into the interior of the housing.

FIGS. 1 and 3 illustrate example air flow paths through the scent diffuser 10 according to the illustrated embodiments. As shown therein, air may be drawn into the interior of the scent diffuser 10 housing through the ventilation apertures 14 extending through the sidewalls of the front body 12 (e.g., by the fan 20). With reference briefly to FIGS. 4A-4B, the fan 20 rotates such that the outer edge of the fan blades 20c are the leading edges of each fan blade, and air is directed along the surface of the each fan blade 20c during rotation and toward the center of the fan 20. In the illustrated embodiment of FIGS. 4A-4B, the fan 20 rotates clockwise within the housing.

The air may then be directed toward a center portion of the scent diffuser 10, and redirected toward the front portion of the scent diffuser 10 by the conical center portion of the fan base plate 20a. The air collides with a back surface of the fragrance reservoir 50 (e.g., a portion of the fragrance reservoir 50 having a wicking surface thereon) to gather fragrance composition to form fragrant air (e.g., through mass transfer of evaporated fragrance composition from the wicking surface to the air passing across the surface of the wicking surface), and the air is redirected toward the sidewalls of the scent diffuser 10. The air is then redirected toward the front portion of the scent diffuser 10 (e.g., by sidewalls of the front body 12, front plate 17, and/or air deflector plate 20b of the fan 20) and out of the scent diffuser 10 through a gap formed between the front plate 17 and trim ring 15.

Although not shown, it should be understood that the direction of rotation of the fan 20 (or the direction of the fan blades 20c within the fan 20) may be reversed in certain embodiments, such that air is pulled through the front portion of the housing and out of the vents defined within the sidewalls of the housing. In such embodiments, the fragrance reservoir 50 may have a wicking material located on sidewalls of the fragrance reservoir 50 or otherwise on portions of the fragrance reservoir 50 located adjacent to and/or within the air travel path.

As shown in the figures, the housing may additionally be configured to securely support a fragrance reservoir 50 therein. As shown in the figures, the fragrance reservoir 50 of the illustrated embodiment is secured within the front body 12, adjacent the fan 20 such that air may be directed from the fan onto the back surface of the fragrance reservoir

50. Specifically, as shown in the figures, the front body 12 may define a hollow body portion having an open back portion (e.g., secured relative to the rear body 11 and an open front portion). The fragrance reservoir 50 may be secured relative to the open front portion, such that a portion of the fragrance reservoir 50 is positioned within the front body 12 adjacent the fan 20, while a portion of the fragrance reservoir 50 is positioned outside of the housing and is visible to a user of the scent diffuser 10. For example, the fragrance reservoir 50 may comprise a transparent and/or translucent material (e.g., a rigid PET), such that a user can see the amount of fragrance composition remaining within the fragrance reservoir 50.

The fragrance reservoir 50 may be detachably secured relative to the housing, such that the fragrance reservoir 50 may be replaced as the fragrance composition therein is diminished and/or when a user desires a new fragrance composition for circulation through the scent diffuser 10. However, it should be understood that the scent diffuser 10 may be entirely disposable in certain embodiments, such that the scent diffuser 10 may be disposed of when the fragrance composition is depleted. In such embodiments, the fragrance reservoir 50 may not be removable from the scent diffuser 10.

In the illustrated embodiment, the fragrance reservoir 50 is secured within a trim ring 15 having a plurality of tabs 16 extending away from the trim ring 15. The fragrance reservoir 50 may be snapped into the trim ring 15, the fragrance reservoir 50 may be adhered relative to a portion of the trim ring 15, and/or the fragrance reservoir 50 may be trapped between a portion of the trim ring 15 and a portion of the scent diffuser housing to secure the fragrance reservoir 50 within the trim ring 15. Although not shown, the fragrance reservoir 50 may be rotatable relative to at least a portion of the trim ring 15. For example, as discussed herein, the fragrance reservoir 50 may have a fragrance intensity adjustment mechanism enabling a user to adjust the amount of wicking surface exposed to the air travel path within the scent diffuser 10, thereby adjusting the intensity of fragrance emitted by the scent diffuser 10. For example, a portion of the fragrance reservoir 50 may be rotatable relative to an adjustment plate on a back portion of the fragrance reservoir 50 (e.g., secured relative to the fragrance reservoir 50 and/or secured relative to the trim ring 15).

The trim ring 15 may be detachably secured within a front plate 17 having an open front surface (e.g., an at least substantially circular open front surface) and an open rear surface (e.g., having a shape corresponding to the shape of the open front surface of the front body 12). The front plate 17 may have receiving apertures defined therein to receive the plurality of tabs 16 therein. By securing the tabs 16 relative to the front plate 17, the trim ring 15 is prevented from rotating relative to the front plate 17 secured therein. Moreover, the tabs 16 space the trim ring 15 (and the fragrance reservoir 50) from the interior walls of the front plate 17, thereby creating a gap between the trim ring 15 and the front plate 17 that serves as an air exhaust vent for the scent diffuser 10. As shown in the attached figures, each of the tabs 16 may have an equal length, such that the trim ring 15 and fragrance reservoir 50 are positioned at least substantially concentric with the front plate 17.

Moreover, the front plate 17 is detachably secureable relative to the front body 12 (e.g., via one or more interference securing components) to thereby secure the front plate 17, trim ring 15, and fragrance reservoir 50 relative to the front body 12 and adjacent the fan 20, such that air circulated by the fan 20 passes adjacent the fragrance reservoir 50 to move evaporated, atomized, sublimated, and/or the like fragrance composition through the fan 20. However, it should be understood that the front plate 17 may be permanently secured relative to the front body 12 and/or integrally formed with the front body 12. In such embodiments, the scent diffuser 10 may be disposable when the fragrance composition within the fragrance reservoir 50 is depleted, as discussed herein.

To emit fragrance composition into the stream of air circulated by the fan 20, the fragrance reservoir 50 defines a wicking surface positioned adjacent the fan 20 when secured within the scent diffuser 10. Collectively, the fragrance reservoir 50 comprises a nonporous and rigid fragrance cup (e.g., a transparent or translucent plastic such as a PET plastic material) having a closed end and an open opposite end. The open opposite end is covered with a wicking surface (e.g., a fabric membrane material, a paper membrane material, a polyethylene membrane material, and/or the like) that wicks fragrance composition from the interior of the fragrance reservoir 50 to an outer surface of the wicking surface to enable the fragrance composition to evaporate into air passing over the wicking material (e.g., while the fan is directing air across the surface of the wicking surface) to form fragrant air. In various embodiments, the wicking surface prevents a liquid fragrance composition from flowing through the wicking surface such that the liquid fragrance composition does not drip out of the fragrance reservoir 50 when the fragrance composition is in a liquid form and in contact with the interior surface of the wicking surface. The wicking surface may be exposed across the entirety of the rear surface of the fragrance reservoir 50, or the wicking material may be exposed on only a portion of the rear surface of the fragrance reservoir 50. In the latter embodiment, a nonporous material may cover a portion of the rear surface of the fragrance reservoir 50 (e.g., external to the wicking surface) such that only a portion of the rear surface of the fragrance reservoir 50 (and the wicking surface) is exposed to air directed from the fan 20. As discussed above, the amount of exposed wicking surface may be adjustable to adjust the intensity of fragrance circulated by the scent diffuser 10. For example, the nonporous material may have a ventilation aperture therein (through which the wicking surface is exposed to the air moving within the scent diffuser 10), and the ventilation aperture may be adjustable in size. For example, a user may irreversibly enlarge the size of the ventilation aperture (e.g., by removing portions of the nonporous material, such as prescored portions of the nonporous material), or the user may reversibly enlarge the size of the ventilation aperture using an adjustment mechanism. For example, the ventilation aperture may be defined through respective ventilation apertures extending through each of two nonporous plates movable relative to one another (e.g., rotatable relative to one another). In a first configuration, the ventilation apertures of the respective movable plates may be aligned with one another to provide a maximum size of the collectively formed ventilation aperture (and according a maximum amount of exposed wicking surface). In a second configuration, the ventilation apertures of the respective movable plates may be only partially aligned to provide a minimum size of the collectively formed ventilation aperture (and accordingly a minimum amount of exposed wicking surface). As discussed herein, the amount of exposed wicking surface may be adjustable by rotating at least a portion of the fragrance reservoir 50 within the trim ring 15.

Moreover, the fragrance reservoir 50 may comprise a removable foil liner positioned over the wicking surface during transportation. The foil liner may prevent fragrance composition from evaporating out of the fragrance reservoir 50 when not installed in a scent diffuser 10. Accordingly, a user may remove the foil liner prior to installing the fragrance reservoir 50 within the scent diffuser 10.

Collectively, the scent diffuser 10 of the illustrated embodiment comprises a power supply, an air circulator, and a fragrance reservoir 50 secured within a single housing. The power supply comprises a solar cell 41 on a back support surface of the scent diffuser 10, and configured to collect light energy (e.g., sunlight) through a support surface on which the scent diffuser 10 is secured. The fragrance reservoir 50 is positioned within a front portion of the scent diffuser 10 (opposite the solar cell 41), and the scent diffuser 10 defines one or more exhaust vents through the front portion to enable air with evaporated fragrance composition to be exhausted out of the front portion of the scent diffuser 10, around the fragrance reservoir 50. The fragrance reservoir 50 is positioned at least substantially concentrically with a fan 20 (and motor 21) of the air circulator, which is configured to pull air through intake vents extending through sidewalls of the scent diffuser 10 and to direct air at and around the fragrance reservoir 50 and ultimately through the exhaust vents of the scent diffuser 10.

Operation of a Scent Diffuser

The scent diffuser 10 may be configured to operate to circulate air past the fragrance reservoir 50, thereby moving evaporated fragrance composition as a portion of generated fragrant air through an environment surrounding the scent diffuser 10 (e.g., an automobile interior).

As discussed herein, the scent diffuser 10 may be secured relative to an interior surface of a window by sticking portions of the tacky plate 43 of the back support surface of the scent diffuser 10 against the interior surface of the window, such that the solar cell 41 is positioned adjacent the window to collect light energy (e.g., from sunlight) that diffuses through the window). As the solar cell 41 captures light energy, the solar cell 41 converts energy within the received light into electrical energy to be stored by the electrical storage device 40. In certain embodiments, once the electrical storage device 40 is charged beyond a threshold charge level (as monitored by the controller circuit 30), the controller circuit 30 closes an electrical circuit between the electrical storage device 40 and the motor 21 and to cause the motor 21 to rotate the fan 20 until the electrical energy level within the electrical storage device 40 reaches a predefined level (e.g., the electrical energy within the electrical storage device 40 is incapable of powering the motor 21). The solar cell 41 then begins recharging the electrical storage device 40 until the electrical storage device 40 is once again charged beyond the threshold charge level. As a non-limiting example, the motor 21 may run for at least approximately 2 minutes on a single charge of the electrical storage device 40, and the solar cell 41 may recharge the electrical storage device 40 beyond the threshold charge level in at least approximately 1 hour when exposed to consistent, direct sunlight.

In certain embodiments, once the electrical storage device 40 is sufficiently charged to power the controller circuit 30 and the motor 21 (e.g., charged beyond a threshold charge level), the controller circuit 30 cycles the motor 21 on and off according to programmed activation parameters defining a predefined criteria for deactivating the motor 21 (e.g., according to a periodic activation schedule according to which the motor 21 is activated for a predefined activation interval (e.g., 15 seconds, 30 seconds, 1 minute, 2 minutes, and/or the like) between defined waiting intervals (e.g., 15 minutes, 1 hour, 2 hours, and/or the like)). During an activation interval, the controller circuit 30 closes an electrical circuit between the electrical storage device 40 and the motor 21 (e.g., according to digital or analog motor rotational speed controls) to cause the motor 21 to rotate the fan 20. The fan 20 thereby draws input air through one or more ventilation apertures 14, past the wicking surface of the fragrance reservoir 50 to form fragrant air (e.g., comprising evaporated fragrance composition, sublimated fragrance composition, atomized fragrance composition, and/or the like), and out of one or more outflow apertures. The movement of the air through the scent diffuser 10 causes movement of air through an environment surrounding the scent diffuser 10, thereby circulating scented air through the environment surrounding the scent diffuser 10.

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A scent diffuser configured to be secured relative to a support surface and to circulate fragrance throughout a surrounding environment, the scent diffuser comprising:
   a housing comprising a support face, an at least partially open front portion opposite the support face, and one or more sidewalls extending between the support face and the at least partially open front portion, wherein the one or more sidewalls have at least one intake aperture extending therethrough;
   a powered air circulator configured for directing air and a fragrance composition through the at least partially open front portion; and
   a solar cell positioned within the support face of the air circulator,
      wherein the support face is configured to secure the scent diffuser relative to the support surface and has a portion configured to allow light to contact the solar cell, and
      wherein the solar cell is configured to convert energy from the light into electrical energy for use by the powered air circulator.

2. The scent diffuser of claim 1, wherein the support face comprises at least one tacky portion configured to detachably adhere the scent diffuser to the support surface.

3. The scent diffuser of claim 2, wherein the tacky portion is configured to adhere the scent diffuser to a substantially vertical surface.

4. The scent diffuser of claim 2, wherein the tacky portion comprises polyurethane.

5. The scent diffuser of claim 1, wherein:
   the housing is configured to store a fragrance composition therein; and
   the air circulator is configured to intake air into the housing through the at least one intake aperture and to flow the intake air over at least a portion of the fragrance composition to produce fragrant outflow air and to substantially flow the fragrant outflow air through the at least partially open front portion.

6. The scent diffuser of claim 5, wherein the air circulator comprises a motorized fan.

7. The scent diffuser of claim 5, wherein the fragrance composition is stored within a fragrance reservoir comprising a wicking surface, wherein the fragrance reservoir is positioned at least partially within the housing, and wherein the wicking surface is configured to allow the fragrance composition to evaporate therefrom into the intake air.

8. The scent diffuser of claim 1, further comprising an electrical storage device in electrical connection with the powered air circulator, and wherein the solar cell is configured to provide electric current for charging the electrical storage device.

9. The scent diffuser of claim 8, further comprising a controller circuit configured to:
monitor a charge level of the electrical storage device; and
upon detecting that the charge level of the electrical storage device satisfies a charge criteria, close an electrical circuit between the electrical storage device and the powered air circulator to activate the powered air circulator.

10. The scent diffuser of claim 9, wherein the controller circuit is configured to maintain the electrical circuit in the closed configuration until the charge level of the electrical storage device meets a predefined threshold.

11. A scent diffuser comprising:
a housing comprising one or more sidewalls and an at least partially open front portion, wherein the one or more sidewalls have at least one intake aperture extending therethrough;
a fragrance reservoir for storing fragrance composition positioned at least partially within the housing, wherein the fragrance reservoir comprises a wicking surface configured to allow the fragrance composition to evaporate from the fragrance reservoir; and
a centrifugal fan aligned with the at least one intake aperture, wherein the centrifugal fan is configured to intake air through the at least one intake aperture and to flow the intake air over the wicking surface of the fragrance reservoir to produce fragrant outflow air and to substantially flow the fragrant outflow air between lateral edges of the fragrance reservoir and the interior edges of the at least partially open front portion.

12. The scent diffuser of claim 11, wherein the fragrance composition is a liquid.

13. The scent diffuser of claim 11, further comprising a power supply comprising an electrical storage device configured to supply power to the centrifugal fan.

14. The scent diffuser of claim 13, wherein the housing further defines a support face opposite the front portion, wherein the support face is configured to secure the scent diffuser relative to a support surface; and
wherein the power supply further comprises a solar cell positioned within the support face, wherein the solar cell is configured to convert energy from light contacting the solar cell into electrical energy stored by the electrical storage device.

15. The scent diffuser of claim 14, further comprising a controller circuit configured to:
monitor a charge level of the electrical storage device; and
upon detecting that the charge level of the electrical storage device satisfies a charge criteria, close an electrical circuit between the electrical storage device and the powered air circulator to activate the powered air circulator.

16. The scent diffuser of claim 15, wherein the controller circuit is configured to maintain the electrical circuit in the closed configuration until the charge level of the electrical storage device meets a predefined threshold.

17. The scent diffuser of claim 13, wherein the support face comprises one or more tacky plates configured to detachably secure the scent diffuser against an at least substantially vertical support surface.

18. A scent diffuser comprising:
a housing comprising one or more sidewalls and an at least partially open front portion, wherein the one or more sidewalls have at least one intake aperture extending therethrough;
a fragrance composition stored within the housing; and
a centrifugal fan comprising:
a base plate;
a deflector plate spaced apart from the base plate, wherein the deflector plate is parallel with at least a portion of the base plate and the deflector plate defines an open central portion; and
a plurality of fan blades extending between the base plate and the deflector plate; and
wherein the plurality of fan blades are aligned with the at least one intake aperture; and
wherein the centrifugal fan is configured to intake air through the at least one intake aperture and to flow the intake air over at least a portion of the fragrance composition to produce fragrant outflow air and to substantially flow the fragrant outflow air through the at least partially open front portion.

19. The scent diffuser of claim 18, wherein the plurality of fan blades are configured to draw air into the housing through the at least one intake aperture and between the base plate and the deflector plate.

* * * * *